United States Patent
Nesta et al.

(10) Patent No.: US 9,795,554 B2
(45) Date of Patent: Oct. 24, 2017

(54) ORAL CARE COMPOSITIONS COMPRISING CALCIUM CARBONATE AND A PRESERVATIVE SYSTEM BASED ON BENZYL ALCOHOL OR BENZOIC ACID, AND AN ALKYLENE GLYCOL

(71) Applicant: Colgate-Palmolive Company, New York, NY (US)

(72) Inventors: Jason Nesta, Cedar Knolls, NJ (US); Melissa Martinetti, Bridgewater, NJ (US); Aileen Cabelly, Boonton, NJ (US); James R. Brown, Edison, NJ (US); Suman Chopra, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/647,759

(22) PCT Filed: Dec. 3, 2012

(86) PCT No.: PCT/US2012/067548
§ 371 (c)(1),
(2) Date: May 27, 2015

(87) PCT Pub. No.: WO2014/088536
PCT Pub. Date: Jun. 12, 2014

(65) Prior Publication Data
US 2015/0290112 A1    Oct. 15, 2015

(51) Int. Cl.
| | | |
|---|---|---|
| *A61Q 11/00* | (2006.01) | |
| *A61K 8/21* | (2006.01) | |
| *A61K 8/19* | (2006.01) | |
| *A61K 8/40* | (2006.01) | |
| *A61K 8/86* | (2006.01) | |
| *A61K 8/34* | (2006.01) | |
| *A61K 8/368* | (2006.01) | |
| *A61K 8/44* | (2006.01) | |
| *A61K 8/25* | (2006.01) | |
| *A61K 8/73* | (2006.01) | |

(52) U.S. Cl.
CPC .................. *A61K 8/86* (2013.01); *A61K 8/19* (2013.01); *A61K 8/25* (2013.01); *A61K 8/34* (2013.01); *A61K 8/345* (2013.01); *A61K 8/368* (2013.01); *A61K 8/44* (2013.01); *A61K 8/731* (2013.01); *A61Q 11/00* (2013.01); *A61K 2800/30* (2013.01); *A61K 2800/33* (2013.01); *A61K 2800/524* (2013.01)

(58) Field of Classification Search
USPC .............................................. 424/49, 401, 52
See application file for complete search history.

(56) References Cited

U.S. PATENT DOCUMENTS

| | | | | |
|---|---|---|---|---|
| 3,622,662 | A | * | 11/1971 | Roberts .................... A61K 8/24 424/54 |
| 3,966,863 | A | | 6/1976 | Forward et al. |
| 3,980,767 | A | | 9/1976 | Chown et al. |
| 3,984,537 | A | | 10/1976 | Harrison et al. |
| 4,328,205 | A | | 5/1982 | Taylor |
| 4,358,437 | A | | 11/1982 | Duke |
| 4,728,508 | A | | 3/1988 | Hayes et al. |
| 2008/0267891 | A1 | * | 10/2008 | Zaidel ....................... A61K 8/04 424/50 |
| 2009/0202450 | A1 | | 8/2009 | Prencipe et al. |
| 2009/0202451 | A1 | | 8/2009 | Prencipe et al. |
| 2012/0141588 | A1 | | 6/2012 | Chopra et al. |
| 2013/0064779 | A1 | | 3/2013 | Yamane et al. |
| 2013/0224270 | A1 | | 8/2013 | Robinson et al. |

FOREIGN PATENT DOCUMENTS

| | | | |
|---|---|---|---|
| GB | 1329254 | * | 9/1973 |
| JP | 2003-226628 A | | 8/2003 |
| RU | 2203032 C1 | | 4/2003 |
| WO | WO 00/78270 | | 12/2000 |

OTHER PUBLICATIONS

Anderson et al., 1967, "The distribution and activity of benzoic acid in some emulsified systems," J. Soc. Cosmetic Chemists, 18:207-214.
Crowley, 2005, "Chapter 39: Solutions, Emulsions, Suspensions, and Extracts," The Science and Practice of Pharmacy, pp. 745-775.
International Search Report and Written Opinion in International Application No. PCT/US2012/067548, mailed Aug. 9, 2013.
Steinberg, 2006, Preservatives for Cosmetics, Second edition, p. 102.
Written Opinion in Interational Application No. PCT/US2012/067548, mailed Nov. 11, 2014.

* cited by examiner

*Primary Examiner* — Lezah Roberts

(57) ABSTRACT

Disclosed herein are oral care compositions comprising an orally acceptable vehicle, calcium carbonate and a preservative system comprising benzyl alcohol, benzoic acid or a salt of benzoic acid; and an alkylene glycol.

33 Claims, No Drawings

ORAL CARE COMPOSITIONS COMPRISING CALCIUM CARBONATE AND A PRESERVATIVE SYSTEM BASED ON BENZYL ALCOHOL OR BENZOIC ACID, AND AN ALKYLENE GLYCOL

BACKGROUND

There is a need to provide paraben free preservative systems without compromising the efficacy of compositions used to treat dental hypersensitivity and the tooth surface adhesion properties thereof. The compositions of the present invention are directed, in part, to these ends.

SUMMARY

In some embodiments, the present invention provides an oral care composition comprising an orally acceptable vehicle, a basic amino acid in free or salt form, particles of precipitated calcium carbonate and a preservative system comprising at least one alkylene glycol.

Optionally, the alkylene glycol comprises propylene glycol.

Optionally, the alkylene glycol is present in an amount of from 2 to 12 wt % based on the weight of the oral care composition, further optionally from 4 to 10 wt % based on the weight of the oral care composition, yet further optionally from 5 to 7 wt % based on the weight of the oral care composition.

Optionally, the preservative system further comprises at least one of benzyl alcohol, benzoic acid and a salt of benzoic acid. The preservative system may therefore include a benzoic acid or a precursor thereof. Further optionally, the preservative system comprises at least one of benzyl alcohol, benzoic acid and a salt of benzoic acid in an amount of from 0.1 to 0.5 wt % based on the weight of the oral care composition, typically from 0.2 to 0.4 wt % based on the weight of the oral care composition, more typically from 0.25 to 0.35 wt % based on the weight of the oral care composition.

Preferably, the preservative system does not comprise any paraben compound. The composition is therefore optionally free from paraben compounds.

Optionally, the particles of precipitated calcium carbonate are present in an amount of from 10 to 50 wt % based on the weight of the oral care composition, further optionally from 25 to 40 wt % based on the weight of the oral care composition.

Optionally, the particles of precipitated calcium carbonate have an average particle size of no greater than a dentin tubule of a mammalian tooth. Typically, the particles of precipitated calcium carbonate have a particle size ranging from 0.1 to 13 microns.

Optionally, the particles of precipitated calcium carbonate comprises a mixture of first particles having a particle size range of from 0.1 to 13 microns and second particles having a particle size range of from 1 to 5 microns. In some embodiments, the first particles have a d50 of from about 2.5 to about 6 microns. In some embodiments, the first particles have a d50 of from 2.5 to 6 microns. In some embodiments, the second particles have a d50 from about 2.2 to about 2.6 microns. In some embodiments, the second particles have a d50 from 2.2 to 2.6 microns.

Typically, the first particles are present in an amount of from 5 to 20 wt % based on the weight of the oral care composition and the second particles are present in an amount of from 5 to 40 wt % based on the weight of the oral care composition. More typically, the first particles are present in an amount of from 5 to 15 wt % based on the weight of the oral care composition and the second particles are present in an amount of from 20 to 30 wt % based on the weight of the oral care composition.

Optionally, the basic amino acid in free or salt form comprises arginine bicarbonate.

Optionally, the basic amino acid in free or salt form is present in an amount of from 5 to 15 wt % based on the weight of the oral care composition, further optionally from 7 to 12 wt % based on the weight of the oral care composition.

Optionally, the oral care composition further comprises silica particles which have an average particle size of no greater than a dentin tubule of a mammalian tooth. Typically, the silica particles have an average particle size of from 1 to 5 microns. Optionally, the silica particles are present in an amount of from 2 to 10 wt % based on the weight of the oral care composition, further optionally from 3 to 6% by weight, based on the total weight of the oral care composition.

Optionally, the orally acceptable vehicle comprises glycerin which is present in an amount of from 15 to 35 wt % based on the weight of the oral care composition, further optionally from 20 to 30 wt % based on the weight of the oral care composition.

Optionally, the orally acceptable vehicle comprises at least one cellulose polymer selected from one or more of hydroxypropylmethyl cellulose (HPMC), hydroxyethylpropyl cellulose (HEPC), hydroxybutylmethyl cellulose (HBMC), and carboxymethyl cellulose (CMC). Typically, the at least one cellulose polymer is present in an amount of from 0.5 to 2.5 wt % based on the weight of the oral care composition, more typically from 1 to 2 wt % based on the weight of the oral care composition.

Optionally, the oral care composition does not comprise any fluorine or fluoride compound and does not comprise any surfactant, in particular any anionic surfactant, in particular sodium lauryl sulfate.

Typically, the composition is prepared in the form of a paste or a gel.

Preferably, the composition is formulated into a form adapted to be applied undiluted within the oral cavity directly to the surface of a mammalian tooth and to be retained within the cavity on the surface for a period of time necessary for treating or preventing hypersensitivity of the tooth. In some embodiments, the composition is retained on an oral cavity surface for greater than 15 seconds. In some embodiments, the composition is retained on an oral cavity surface for from about 15 seconds to about 15 minutes. In some embodiments, the composition is retained on an oral cavity surface for from about 30 seconds to about 10 minutes. In some embodiments, the composition is retained on an oral cavity surface for from about 1 minute to about 5 minutes. In some embodiments, the composition is retained on an oral cavity surface for about 1 minute.

The invention further provides a method of reducing dental sensitivity comprising applying an oral care composition of the invention to the surface of a mammalian tooth.

The invention further provides a method of occluding a dentin tubule within the surface of a mammalian tooth comprising applying to the tooth surface a composition according to the invention.

The invention further provides the use, in an oral care composition according to the invention, of propylene glycol in an amount of from 5 to 7 wt % based on the weight of the oral care composition, as a preservative and for enhancing the adhesion of the oral care composition to the tooth surface when used in a method of reducing dental sensitivity, or occluding a dentin tubule within the surface of a mammalian tooth, by applying the composition to the surface of a mammalian tooth.

The compositions may contain additional therapeutic and non-therapeutic components, and may also be utilized in the practice of various methods, all of which are included within the scope of the invention. The composition and methods within the scope of the invention may be useful in, for example, reducing or eliminating tooth sensitivity of a mammal, improving/maintaining systemic health, and/or occluding dentin tubules.

The present invention is predicated on the finding by the present inventors that in an oral care composition comprising a basic amino acid in free or salt form and particles of precipitated calcium carbonate for treating or relieving hypersensitivity, a composition can be formulated for use as a "leave-on" oral care composition which can be applied to the tooth surface and can be left within the oral cavity for an extended period of time without causing fluoride damage to the teeth or irritation from a surfactant.

Further, the compositions can be formulated to have a viscosity and rheology so that they can be dispensed directly in an undiluted form onto a tooth surface using an applicator in order to provide relief against dental hypersensitivity, such as a dispenser extruding a narrow cross-section extrudate of the composition.

Still further, the incorporation of an alkylene glycol, such as propylene glycol, optionally combined with benzyl alcohol or a precursor of benzoic acid, into the composition can provide a preservative system with high efficacy antimicrobial against molds/fungi. Since these compositions may be employed in an applicator which is used, periodically over an extended period of time, to dispense a dose of the composition stored in the applicator into the oral cavity, and therefore the dispensing end of the applicator may come into direct contact with the oral cavity, it is important that the compositions have high antimicrobial preservation efficacy against bacteria and molds/fungi.

DETAILED DESCRIPTION

It should be understood that the detailed description and specific examples, while indicating embodiments of the invention, are intended for purposes of illustration only and are not intended to limit the scope of the invention.

As referred to herein, all compositional percentages are by weight of the total composition, unless otherwise specified.

The invention described herein includes an oral care composition comprising an orally acceptable vehicle, a basic amino acid in free or salt form, particles of precipitated calcium carbonate and a preservative system comprising at least one alkylene glycol.

The invention further provides a method of reducing dental sensitivity comprising applying an oral care composition of the invention to the surface of a mammalian tooth.

The invention further provides a method of occluding a dentin tubule within the surface of a mammalian tooth comprising applying to the tooth surface a composition according to the invention.

The invention further provides the use, in an oral care composition according to the invention, of propylene glycol in an amount of from 5 to 7 wt % based on the weight of the oral care composition, as a preservative and for enhancing the adhesion of the oral care composition to the tooth surface when used in a method of reducing dental sensitivity, or occluding a dentin tubule within the surface of a mammalian tooth, by applying the composition to the surface of a mammalian tooth.

The present invention is at least partly based on the finding by the present inventors that alkylene glycol may have efficacy as a preservative, with particularly high efficacy against molds/fungi, in the composition of the invention comprising a system for relieving dentin hypersensitivity which includes a basic amino acid in free or salt form and particles of precipitated calcium carbonate.

Typically, the alkylene glycol comprises propylene glycol. Optionally, the alkylene glycol is present in an amount of from 2 to 12 wt %, or from 4 to 10 wt %, or from 5 to 7 wt %, based on the weight of the oral care composition.

Optionally, the preservative system further comprises at least one of benzyl alcohol, benzoic acid and a salt of benzoic acid. Further optionally, the preservative system comprises at least one of benzyl alcohol, benzoic acid and a salt of benzoic acid in an amount of from 0.1 to 0.5 wt %, or from 0.2 to 0.4 wt %, or from 0.25 to 0.35 wt %, based on the weight of the oral care composition.

Preferably, the preservative system does not comprise any paraben compound.

As stated above, the system for relieving dentin hypersensitivity includes a basic amino acid in free or salt form and particles of precipitated calcium carbonate Optionally, the particles of precipitated calcium carbonate are present in an amount of from 10 to 50 wt %, or from 25 to 40 wt %, based on the weight of the oral care composition.

Optionally, the particles of precipitated calcium carbonate have an average particle size of no greater than a dentin tubule of a mammalian tooth. Typically, the particles of precipitated calcium carbonate have a particle size ranging from 0.1 to 13 microns.

Optionally, the particles of precipitated calcium carbonate comprises a mixture of first particles having a particle size range of from 0.1 to 13 microns and second particles having a particle size range of from 1 to 5 microns. In some embodiments, the first particles have a d50 of from about 2.5 to about 6 microns. In some embodiments, the first particles have a d50 of from 2.5 to 6 microns. In some embodiments, the second particles have a d50 from about 2.2 to about 2.6 microns. In some embodiments, the second particles have a d50 from 2.2 to 2.6 microns.

Typically, the first particles are present in an amount of from 5 to 20 wt % based on the weight of the oral care composition and the second particles are present in an amount of from 5 to 40 wt % based on the weight of the oral care composition. More typically, the first particles are present in an amount of from 5 to 15 wt % based on the weight of the oral care composition and the second particles are present in an amount of from 20 to 30 wt % based on the weight of the oral care composition.

Optionally, the basic amino acid in free or salt form comprises arginine bicarbonate.

Optionally, the basic amino acid in free or salt form is present in an amount of from 5 to 15 wt %, or from 7 to 12 wt %, based on the weight of the oral care composition.

Optionally, the oral care composition further comprises silica particles which have an average particle size of no greater than a dentin tubule of a mammalian tooth. Such silica particles may be included for relieving dentin hypersensitivity. Typically, the silica particles have an average particle size of from 1 to 5 microns. Optionally, the silica particles are present in an amount of from 2 to 10 wt %, or from 3 to 6% by weight, based on the total weight of the oral care composition.

The compositions may contain additional therapeutic and non-therapeutic components, and may also be utilized in the practice of various methods, all of which are included within the scope of the invention. The composition and methods within the scope of the invention may be useful in, for example, reducing or eliminating tooth sensitivity of a mammal, improving/maintaining systemic health, and/or occluding dentin tubules.

The oral compositions of the invention also include a polymeric adherent material to assist in the retention of the calcium carbonate particles, and, if present, the silica particles, within the dentin tubules under salivary flow and during exposure to acidic foods and beverages.

The polymeric adherent material may be any known or to be developed in the art that attaches to the surface of a mammalian tooth and/or to the heterogeneous biofilm which also may be present on a tooth's surface. Attachment may occur by any means, such as ionic interaction, van der Waals forces, hydrophobic-hydrophilic interactions, etc. The adherent material may be, for example, any homopolymers or copolymers (hereinafter referred to collectively as a "polymers") that adhere to the surface of a tooth. Such polymers may include cellulose polymers, for example one or more hydroxyalkyl cellulose polymers, such as hydroxypropylmethyl cellulose (HPMC), hydroxyethylpropyl cellulose (HEPC), hydroxybutylmethyl cellulose (HBMC), carboxymethyl cellulose (CMC).

In one embodiment the polymeric adherent material comprises a mixture of cellulose materials, for example a mixture of two hydroxyalkyl cellulose materials having different molecular weight.

The polymers may alternatively or additionally include poly (ethylene oxide) polymers (such as POLYOX from Dow Chemical), linear PVP and cross-linked PVP, PEG/PPG copolymers (such as BASF Pluracare L1220), ethylene oxide (EO)-propylene oxide (PO) block copolymers (such as polymers sold under the trade mark Pluronic available from BASF Corporation), ester gum, shellac, pressure sensitive silicone adhesives (such as BioPSA from Dow-Corning), methacrylates, or mixtures thereof. In an embodiment, a copolymer comprises (PVM/MA). In an embodiment, a copolymer comprises poly (methylvinylether/maleic anhydride). In another embodiment, a copolymer comprises poly (methylvinylether/maleic acid). In another embodiment, a copolymer comprises poly (methylvinylether/maleic acid) half esters. In another embodiment, a copolymer comprises poly (methylvinylether/maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average).

Optionally, the orally acceptable vehicle comprises at least one cellulose polymer selected from one or more of hydroxypropylmethyl cellulose (HPMC), hydroxyethylpropyl cellulose (HEPC), hydroxybutylmethyl cellulose (HBMC), and carboxymethyl cellulose (CMC). Typically, the at least one cellulose polymer is present in an amount of from 0.5 to 2.5 wt % based on the weight of the oral care composition, more typically from 1 to 2 wt % based on the weight of the oral care composition.

Commercially-available polymers may be used in the present invention. It is understood that over time, the exact size, weight and/or composition of a commercially-available polymer may change. Based on the disclosure set forth herein, the skilled artisan will understand how to determine whether such polymers are useful in the invention.

The oral care composition may in particular be a dentifrice composition which may be a toothpaste or a gel. Typically, the composition is formulated as a "leave-on" composition which can be applied undiluted and left in the oral cavity for an extended period of time. Such a composition does not include any components or additives which would cause damage or irritation to the oral cavity.

Optionally, the oral care composition does not comprise any fluorine or fluoride compound and does not comprise an anionic surfactant, in particular sodium lauryl sulfate.

Preferably, the composition is formulated into a form adapted to be applied undiluted within the oral cavity directly to the surface of a mammalian tooth and to be retained within the cavity on the surface for a period of at least 1 hour for treating or preventing hypersensitivity of the tooth.

The composition according to the present invention may also comprise one or more further agents typically selected from an anti-plaque agent, a whitening agent, antibacterial agent, cleaning agent, a flavouring agent, a sweetening agent, adhesion agents, surfactants, foam modulators, abrasives, pH modifying agents, humectants, mouth feel agents, colorants, abrasive, tartar control (anticalculus) agent, saliva stimulating agent, nutrient and combinations thereof. The dentifrice composition according to the present invention comprises an orally acceptable vehicle in a product such as a toothpaste or a gel. As used herein, an "orally acceptable vehicle" refers to a material or combination of materials that are safe for use in the compositions of the present invention, commensurate with a reasonable benefit/risk ratio.

Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

The oral care compositions described herein may be formulated into any delivery form that permits contact of the adherent material and the particles, to the tooth surface. For example, the compositions may be formulated into a mouth rinse, a paste, a gel, a lozenge (dissolvable or chewable), a spray, a gum, and a film (wholly or partially dissolvable, or indissoluble). The composition may contain any conventional excipients or carriers, although these will vary depending on the dosage form or means of dosage selected.

Excipients or carriers can include, for example, humectants, colorants, flavorants, glycerin, sorbitol, xylitol, water or other solvents, gum bases, thickening agents, surfactants, carrageenan (rich moss), xanthan gum and sodium carboxymethyl cellulose, starch, polyvinyl pyrrolidone, hydroxyethyl propyl cellulose, hydroxybutyl methyl cellulose, hydroxypropyl methyl cellulose, and hydroxyethyl cellulose and amorphous silicas.

Optionally, the orally acceptable vehicle comprises glycerin which is present in an amount of from 15 to 35 wt % based on the weight of the oral care composition, further optionally from 20 to 30 wt % based on the weight of the oral care composition.

The oral care composition of the invention may be prepared by any means known in the art. For example, preparation methods for dentifrices are well known, for example, as described in U.S. Pat. No. 3,966,863; U.S. Pat. No. 3,980,767; U.S. Pat. No. 4,328,205; and U.S. Pat. No. 4,358,437, the contents of which are incorporated herein by reference. In general, any humectant (e.g., glycerin, sorbitol, propylene glycol, and/or polyethylene glycol) is dispersed in water in a conventional mixer under agitation. Into that dispersion are added the thickeners, such as carboxylmethyl cellulose (CMC), carrageenan, or xanthan gum; any anionic polycarboxylate; any salts, such as sodium fluoride anticaries agents; and any sweeteners.

The resultant mixture is agitated until a homogeneous gel phase is formed. Into the gel phase are added any pigments utilized, such as $TiO_2$, and additionally any acid or base required to adjust the pH of the composition. These ingredients are mixed until a homogeneous phase is obtained.

The mixture is then transferred to a high speed/vacuum mixer, wherein the surfactant ingredients are added to the mixture. The calcium carbonate particles and any silica particles utilized are added subsequently. Any water insoluble agents, such as triclosan, are solubilized in the flavor oils to be included in the dentifrice, and that solution is added to the mixture, which is then mixed at high speed in the range from 5 to 30 minutes, under a vacuum of 20 to 50 mm of Hg. The resultant product is a homogeneous, semi-solid, extrudable paste or gel product.

The oral care composition according to the present invention may be administered to or applied to a human or other animal subject. The composition is suitable for administration or application to the oral cavity of a human or animal subject.

In an embodiment, the amino acid and calcium carbonate particle-containing composition may be applied to the tooth via conventional brushing techniques (e.g., use of a toothbrush). In another embodiment, such a composition may be applied to the tooth via a method other than conventional brushing techniques. Other methods of application include manual application (e.g., applying a composition to a tooth using one or more fingers, rubbing onto the tooth surface, rubbing in a circular motion, etc. . . . ), or application using any known dental appliance or applicator. It will be understood, based on the disclosure set forth herein, that any method of smearing a composition onto a tooth, optionally using varying degrees of physical pressure, is encompassed by the invention.

Desensitization of a tooth according to the invention may be measured by any technique set forth herein, or any technique known to the skilled artisan.

Application of the composition to the tooth surface results in the introduction of the composition into one or more dentin tubules. The composition is applied to the teeth by any method set forth herein or known in the art.

The invention also includes within its scope several related methods. For example, the invention includes within its scope methods of reducing and methods of occluding a dentin tubule of a mammalian tooth, methods of protecting dentin from acid-mediated degradation, and methods of reducing dental sensitivity.

Each of these methods includes the steps of applying any of the compositions described above to the tooth surface. Application may be carried out by any method, so long as the adherent material and the particles are placed in contact with the tooth surface. Application may be accomplished by brushing, flossing, prophylaxis, irrigating, wiping, rinsing (lavage of oral cavity), foam/gel and in-tray application, masticating, spraying, painting, etc., or applied by film or strip.

Dental sensitivity may be reduced according to a method of the invention by applying a composition of the invention to a tooth surface. A composition may be applied using a traditional method, as described in detail elsewhere herein, or by any appliance or applicator, whether or not typically associated with dental use. In an embodiment, one or more human fingers is used to apply a dental sensitivity-reducing composition to one or more teeth. A finger can be used to smear the composition on the surface of a tooth, or to otherwise apply the composition to the surface of a tooth.

The application may be at least once a day, although up to five times per day may be preferred, and may be carried out over a duration of time, e.g., one week, up to one year, up to three years or for a lifetime.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1 and Comparative Examples 1 and 2

Dentifrice compositions having the formula of Table 1 are prepared.

The compositions all include arginine bicarbonate and precipitated calcium carbonate. However, the compositions differ with regard to their preservative systems.

In particular, in Example 1 the composition comprised 0.3 wt % benzyl alcohol and 7.0 wt % propylene glycol. In contrast, in Comparative Example 1 the composition comprised no benzyl alcohol or propylene glycol but instead comprised 0.1 wt % methyl paraben and 0.02 wt % propyl paraben as conventional preservatives. In contrast, in Comparative Example 2 the composition comprised 0.3 wt % benzyl alcohol instead of the 0.1 wt % methyl paraben and 0.02 wt % propyl paraben used in Comparative Example 1 and also comprised no propylene glycol.

None of these compositions comprised any surfactant, and in particular did not comprise any anionic surfactant, such as sodium lauryl sulfate. Furthermore, none of these compositions comprised any fluoride compound. Accordingly, the compositions were suitable for use as a "leave-on" oral care composition which can be applied to the tooth surface and can be left within the oral cavity for the necessary period of time.

Further, the compositions are formulated to have a viscosity and rheology so that they can be dispensed directly in an undiluted form onto a tooth surface using an applicator in order to provide relief against dental hypersensitivity, such as a dispenser extruding a narrow cross-section extrudate of the composition. The binder system to provide such viscosity and rheology includes sodium carboxymethyl cellulose.

TABLE 1

| Ingredient | Ex. 1 | Comp. Ex. 1 | Comp. Ex. 2 |
|---|---|---|---|
| Glycerin | 24.6 | 24.6 | 24.6 |
| Sodium CMC | 1.5 | 1.5 | 1.5 |
| Sodium saccharin | 0.3 | 0.3 | 0.3 |

TABLE 1-continued

| Ingredient | Ex. 1 | Comp. Ex. 1 | Comp. Ex. 2 |
|---|---|---|---|
| Sodium bicarbonate | 0.5 | 0.5 | 0.5 |
| N-silicate | 0.8 | 0.8 | 0.8 |
| Titanium dioxide | 0.5 | 0.5 | 0.5 |
| Precipitated calcium carbonate-Light | 10 | 10 | 10 |
| Precipitated calcium carbonate-High Absorption | 25 | 25 | 25 |
| Methyl paraben | — | 0.1 | — |
| Propyl paraben | — | 0.02 | — |
| Benzyl alcohol | 0.3 | — | 0.3 |
| Arginine bicarbonate (70% aq. solution) | 13.86 | 13.86 | 13.86 |
| Propylene glycol | 7.0 | — | — |
| Flavor | 1 | 1 | 1 |
| Water | Balance to 100% | Balance to 100% | Balance to 100% |

Since the compositions may be employed in an applicator which is used, periodically over an extended period of time, to dispense a dose of the composition stored in the applicator into the oral cavity, it is important that the compositions have high preservation efficacy against mold/fungi.

The compositions of Example 1 and Comparative Examples 1 and 2 are evaluated for their ability to resist fungal growth.

The results of the antimicrobial preservation efficacy test against mold, in particular fungi, are shown in Table 2 (below).

TABLE 2

|  | Mold reduction against fungi |
|---|---|
| Example 1-Benzyl alcohol and propylene glycol | >99.9% (no growth) |
| Comparative Example 1-Methyl paraben and propyl paraben | 99.96% |
| Comparative Example 2-Benzyl alcohol | 96.92% |

The composition of Comparative Example 1 included a conventional paraben preservative system.

In Comparative Example 2 the conventional paraben preservative system was replaced by benzyl alcohol.

It may be seen that the composition of Example 1 which includes propylene glycol as well as the benzyl alcohol provided an acceptable level of mold reduction.

The composition of Example 1 which included propylene glycol and benzyl alcohol therefore unexpectedly provided a high antimicrobial preservation efficacy against molds/fungi.

Example 2

The composition of Example 1 which included propylene glycol and benzyl alcohol is tested in an in vitro test to determine the efficacy of occluding dentin tubules. The test measures hydraulic conductance through a sample of dentin incorporating exposed tubules after a single application of the composition to the dentin surface. The composition exhibited an occlusion efficacy of about 80%, as measured by flow reduction, after only one application of the composition, with significant occlusion being exhibited after a period of 2 hours following the single application. The composition was therefore found to provide an anti-hypersensitivity benefit when applied to the surface of a tooth having exposed dentin tubules.

Example 3

An in vitro test is conducted to model the adhesive properties of the compositions to a tooth surface.

The test is conducted as follows: 1. The weight of a glass slide was recorded; 2. A dose of the composition was applied to a surface of the glass slide; 3. The weight of the glass slide and the dose of the composition was recorded; 4. The glass slide was submerged in agitated water for a period of 1 minute; 5. The glass slide was allowed to dry in air; and 6. The final weight of the glass slide and the remaining composition was recorded.

The percentage amount of the composition retained on the glass slide after the immersion test was determined. A number of runs for each composition are conducted to provide a statistically significant result.

The results are shown in Table 3 (below).

TABLE 3

|  | Mean % of Composition Retained |
|---|---|
| Example 1-Benzyl alcohol and propylene glycol | 0.4 |
| Comparative Example 1-Methyl paraben and propyl paraben | 0.3 |
| Comparative Example 2-Benzyl alcohol | 0.3 |

The composition of Example 1 provided a statistically higher adhesion to a hard surface in this modelled system as compared to the compositions of Comparative Examples 1 and 2 and therefore would provide enhanced adhesion to a tooth surface for the purpose of providing hypersensitivity relief.

Therefore the composition of Example 1 provided not only an effective preservative system free of paraben preservatives but also provided enhanced tooth surface adhesion properties as compared to the Comparative Example compositions.

Example 4

Yet further, the composition of Example 1 and the composition of Comparative Examples 1 and 2 were subjected to consumer testing. Consumers tested the three compositions for a period of two weeks, and determined comparative results for the criteria of taste, consistency, ease of spreading onto the tooth surfaces and overall satisfaction with the product. The composition was applied to the teeth in undiluted form for achieving instant relief against hypersensitivity.

The results are shown in Table 4 (below).

TABLE 4

|  | Mean Score for Consumer Satisfaction in Achieving Hypersensitivity Relief |
|---|---|
| Example 1-Benzyl alcohol and propylene glycol | 3.9 |
| Comparative Example 1-Methyl paraben and propyl paraben | 3.6 |
| Comparative Example 2-Benzyl alcohol | 3.8 |

The composition of Example 1 achieved statistically higher scores in all categories as compared to the composition of Comparative Examples 1 and 2. In particular, the addition of the propylene glycol which was found to increase the adhesion of the benzyl alcohol-containing composition to glass slides was correspondingly found to produce an increase in adhesion and retention of the benzyl alcohol-containing composition on the tooth surfaces.

What is claimed is:

1. An oral care composition comprising:
   a preservative system comprising
      benzyl alcohol in an amount of from 0.1 to 0.5 wt % based on the weight of the oral care composition; and
      an alkylene glycol;
   a basic amino acid in free or salt form present in an amount of from 5 to 15 wt %;
   calcium carbonate in an amount of from 10-50% wt % based on the weight of the composition; and
   an orally acceptable vehicle,
   wherein the alkylene glycol is propylene glycol and is present in an amount of from 2 to 12 wt % based on the weight of the oral care composition, and wherein the calcium carbonate is precipitated calcium carbonate.

2. The composition according to claim 1 wherein the alkylene glycol is present in an amount of from 4 to 10 wt % based on the weight of the oral care composition.

3. The composition according to claim 2 wherein the alkylene glycol is present in an amount of from 6 to 8 wt % based on the weight of the oral care composition.

4. The composition according to claim 1 wherein the preservative system comprises benzyl alcohol in an amount of from 0.2 to 0.4 wt % based on the weight of the oral care composition.

5. The composition according to claim 4 wherein the preservative system comprises benzyl alcohol in an amount of from 0.25 to 0.35 wt % based on the weight of the oral care composition.

6. The composition according to claim 1 wherein the preservative system does not comprise any paraben compound.

7. The composition according to claim 1 wherein the calcium carbonate is present in an amount of from 25 to 40 wt % based on the weight of the oral care composition.

8. The composition according to claim 1 wherein the calcium carbonate has a particle size of from 0.1 to 13 microns.

9. The composition according to claim 1 wherein the calcium carbonate comprises a mixture of first particles having a particle size range of from 0.1 to 13 microns and second particles having a particle size range of from 1 to 5 microns.

10. The composition according to claim 9 wherein the first particles are present in an amount of from 5 to 20 wt % based on the weight of the oral care composition and the second particles are present in an amount of from 5 to 40 wt % based on the weight of the oral care composition.

11. The composition according to claim 10 wherein the first particles are present in an amount of from 5 to 15 wt % based on the weight of the oral care composition and the second particles are present in an amount of from 20 to 30 wt % based on the weight of the oral care composition.

12. The composition according to claim 1 wherein the basic amino acid in free or salt form comprises arginine bicarbonate.

13. The composition according to claim 1 wherein the basic amino acid in free or salt form is present in an amount of from 5 to 15 wt % based on the weight of the oral care composition.

14. The composition according to claim 13 wherein the basic amino acid in free or salt form is present in an amount of from 7 to 12 wt % based on the weight of the oral care composition.

15. The composition according to claim 1 further comprising silica particles which have an average particle size of no greater than a dentin tubule of a mammalian tooth.

16. The composition according to claim 15 wherein the silica particles have an average particle size of from 1 to 5 microns.

17. The composition according to claim 15 wherein the silica particles are present in an amount of from 2 to 10 wt % based on the weight of the oral care composition.

18. The composition according to claim 17 wherein the silica particles are present in an amount of from 3 to 6% by weight, based on the total weight of the oral care composition.

19. The composition according to claim 1 wherein the orally acceptable vehicle comprises glycerin which is present in an amount of from 15 to 35 wt % based on the weight of the oral care composition.

20. The composition according to claim 19 wherein the glycerin is present in an amount of from 20 to 30 wt % based on the weight of the oral care composition.

21. The composition according to claim 1 wherein the orally acceptable vehicle comprises at least one cellulose polymer selected from one or more of hydroxypropylmethyl cellulose (HPMC), hydroxyethylpropyl cellulose (HEPC), hydroxybutylmethyl cellulose (HBMC), and carboxymethyl cellulose (CMC).

22. The composition according to claim 21 wherein the at least one cellulose polymer is present in an amount of from 0.5 to 2.5 wt % based on the weight of the oral care composition.

23. The composition according to claim 22 wherein the at least one cellulose polymer is present in an amount of from 1 to 2 wt % based on the weight of the oral care composition.

24. The composition according to claim 1 wherein the oral care composition does not comprise any fluorine or fluoride compound and does not comprise an anionic surfactant.

25. The composition according to claim 24 wherein the oral care composition does not comprise sodium lauryl sulfate.

26. The composition according to claim 1, wherein the oral care composition is substantially surfactant free.

27. The composition according to claim 1 wherein the composition is formulated into a dentifrice in the form of a paste or gel.

28. The composition according to claim 1 wherein the composition is substantially free of pyrophosphates.

29. The composition according to claim 28 wherein the composition is substantially free of polyphosphates.

30. The composition according to claim 1 wherein the composition is formulated into a form adapted to be applied undiluted within the oral cavity directly to the surface of a mammalian tooth and to be retained within the cavity on the surface for a period of at least 1 hour for treating or preventing hypersensitivity of the tooth.

31. The composition according to claim 1, wherein the oral care composition provides a fluid flow rate of no greater than about 45% of the fluid flow rate of etched dentin.

32. A method of reducing dental sensitivity comprising applying to the surface of a mammalian tooth an oral care composition of claim 1.

33. A method of occluding a dentin tubule within the surface of a mammalian tooth comprising applying to the tooth surface a composition according to claim 1.

* * * * *